(12) United States Patent
Choi et al.

(10) Patent No.: US 7,323,161 B2
(45) Date of Patent: Jan. 29, 2008

(54) PATCH FOR TOOTH WHITENING

(75) Inventors: Young Kweon Choi, Seoul (KR); Hyun Suk Yu, Gunpo-si (KR); Jae Soon Ahn, Seoul (KR); Hee Sook Kim, Seoul (KR); Hyun Woo Kim, Gunpo-si (KR)

(73) Assignee: Icure Pharmaceutical Corp., Seoul (KR)

( * ) Notice: Subject to any disclaimer, the term of this patent is extended or adjusted under 35 U.S.C. 154(b) by 390 days.

(21) Appl. No.: 10/729,648

(22) Filed: Dec. 5, 2003

(65) Prior Publication Data

US 2004/0219113 A1 Nov. 4, 2004

(30) Foreign Application Priority Data

Apr. 30, 2003 (KR) .................. 10-2003-0027455
Oct. 10, 2003 (KR) .................. 10-2003-0070707

(51) Int. Cl.
*A61K 8/00* (2006.01)
*A61Q 11/00* (2006.01)
*A61F 13/00* (2006.01)

(52) U.S. Cl. .................. 424/53; 424/401; 424/435; 424/443

(58) Field of Classification Search .................. None
See application file for complete search history.

(56) References Cited

U.S. PATENT DOCUMENTS

| 4,713,243 A * | 12/1987 | Schiraldi et al. ............. 424/676 |
| 5,800,832 A * | 9/1998 | Tapolsky et al. ............. 424/449 |
| 6,585,997 B2 * | 7/2003 | Moro et al. .................. 424/434 |
| 2004/0105834 A1 * | 6/2004 | Singh et al. ............. 424/70.13 |

FOREIGN PATENT DOCUMENTS

| JP | 10017448 | 1/1998 |
| KR | 10-2002-0096264 | 12/2002 |
| KR | 10-2002-0097297 | 12/2002 |
| KR | 10-2002-0097298 | 12/2002 |
| KR | 10-2003-0000299 | 1/2003 |
| KR | 10-2003-0001297 | 1/2003 |
| KR | 10-2003-0003973 | 1/2003 |
| WO | WO 98/55044 | 12/1998 |
| WO | WO 01/68045 A1 * | 9/2001 |

OTHER PUBLICATIONS

Korean Patent Abstracts, Jang, Seok Yun, et al., Patch for Whitening Tooth Surfaces in Which Peroxides are Stabilized, Application No. 10-2001-0034617, Filed Jun. 19, 2001; Published Dec. 31, 2002 under Publication No. 10-2002-0096264.
Korean Patent Abstracts, Jang, Seok Yun, et al. Dry Type Patch for Whitening Tooth Surface, Application No. 10-2001-0034944, Filed Jun. 20, 2001; Published Dec. 31, 2002 under Publication No. 10-2002-0097297.
Korean Patent Abstracts, Jang, Seok Yun, et al. Patch for Whitening Tooth Surface With Improved Properties of Use, Application No. 10-2001-0034945 Filed Jun. 20, 2001; Published Dec. 31, 2002 under Publication No. 10-2002-0097298.
Korean Patent Abstracts, Jang, Seok Yun, et al. Semi-Opaque Teeth Whitening Patch, Application No. 10-2001-0036025, Filed Jun. 23, 2001; Published Jan. 6, 2003 under Publication No. 10-2003-0000299.
Korean Patent Abstracts, Jang, Seok Yun, et al. Patch for Whitening Teeth Comprising Several Layers, Application No. 10-2002-0034902, Filed Jun. 21, 2002; Published Jan. 6, 2003 under Publication No. 10-2003-0001297.
Korean Patent Abstracts, Jang, Seok Yun, et al., Soft Patch for Whitening Teeth, Application No. 10-2001-0039851, Filed Jul. 4, 2001; Published Jan. 14, 2003 under Publication No. 10-2003-0003973.
Japanese Patent Abstracts, Suzuki, Kunitomo, et al., Application No. JP19960188459 19960628, Patent No. JP10017448 published on Jan. 20, 1998.

* cited by examiner

*Primary Examiner*—Frederick Krass
(74) *Attorney, Agent, or Firm*—Lucas & Mercanti, LLP

(57) ABSTRACT

The patch for tooth whitening of the present invention includes a tooth-adhering layer (1) containing erodible polymer complexes formed by hydrogen bonding of a polymer with a carboxyl group (—COOH) and a polymer with a carbonyl group (—C═O) or ether group (—O—) and a tooth whitening agent; and an erosion rate-controlling layer (2) containing a mixture of a hydrophilic polymer and a film-forming polymer, wherein the patch is in a film form and is characterized by being eroded until extinguished after releasing the tooth whitening agent. When applied to the teeth, the patch releases a peroxide tooth-whitening agent while being hydrated by water in the mouth during a prescribed period, and thereafter, eroded until extinguished, thereby not requiring an additional detaching work from the teeth. Therefore, the patch is convenient in use and greatly reduces an obstruction sensation. Moreover, the patch has an excellent whitening effect.

16 Claims, 1 Drawing Sheet

Tooth

PATCH FOR TOOTH WHITENING

CROSS REFERENCE TO RELATED APPLICATIONS

This application claims the benefit of priority from Korean Patent Application No. 2003-0027455 filed on Apr. 30, 2003 and Korean Patent Application No. 2003-0070707 filed on Oct. 10, 2003. The contents of each of the forgoing applications are incorporated by reference herein.

BACKGROUND OF THE INVENTION

1. Field of the Invention

The present invention relates to a patch for tooth whitening. More particularly, the present invention relates to a patch for tooth whitening, comprising a tooth-adhering layer (1) containing erodible polymer complexes formed by hydrogen bonding of a polymer with a carboxyl group (—COOH) and a polymer with a carbonyl group (—C═O) or ether group (—O—) and a tooth whitening agent; and an erosion rate-controlling layer (2) containing a mixture of a hydrophilic polymer and a film-forming polymer, wherein the patch is in a film form and is characterized by being eroded until extinguished after releasing the tooth whitening agent.

2. Description of the Prior Art

A tooth is composed of an inner dentine layer and an outer hard enamel layer functioning to protect the inner parts of the teeth from infection and decay. The enamel layer is composed of about 96% inorganic matter and about 4% organic matter and water. The inorganic crystals themselves are colorless and transparent. However, spaces exist between the inorganic mineral crystals, which contain organic materials including proteins. Staining substances often penetrate the spaces, thus leading to a yellow staining of the teeth. For this reason, a lot of efforts have been made to make transparent or white teeth.

Among the tooth whitening products currently available, fluoride-containing toothpaste is effective in chemically removing stains on the teeth, which are generated by absorbance of food debris, nicotine, coffee or black tea and the like to the teeth surfaces, or by staining of the tartar or soft precipitates on the teeth surfaces with staining substances. Toothpaste is typically used to obtain a clean feeling in the mouth or to freshen the breath. However, tooth whitening is difficult to be achieved just by brushing the teeth with the toothpaste.

In the 1960's, an American dentist stumbled upon during treating patients with gum disease the fact that hydrogen peroxide used in gum disease treatment bleach the teeth, and developed a tooth-whitening agent that is both effective and safe.

In addition, a first home-usable tooth-whitening apparatus was developed in the end of the 1980's, which uses a night guard generally containing a hydrogen peroxide or carbamide peroxide gel. Currently, such a method is the most popular in tooth whitening. However, since the peroxide gel is used in a high concentration, such a method is problematic with respect to convenience in use and safety, such as the case that gum is irritated by the excessive peroxide gel and a tray.

To solve these problems, various tooth-whitening products have been developed by employing peroxides of low concentrations without use of the mouth tray.

U.S. Pat. Nos. 5,879,691, 5,891,453 and 5,989,569 and International Pat. Publication No. WO98/55044, which are owned or were applied by the Procter & Gamble Company, disclose delivery systems for a tooth-whitening substance, which are characterized by coating a polyethylene film instead of a mouth tray with a carbamide gel containing a peroxide as a tooth whitening agent and then contacting the gel onto a surface of the teeth. These systems have improved simplicity in use in terms of not using the mouth tray. However, such systems, which employed the whitening agent in a gel phase just applied onto the film, have drawbacks in that the peroxide gel is apt to stick to the hands or tongue, gum, etc. upon its application onto the teeth surfaces and the polyethylene film must be removed after a prescribed time.

Japanese Pat. Laid-open Publication No. Heisei. 10-17448, applied by the Lion Company, discloses a mouth-pasting agent of sheet form sheet, comprising kojic acid, kojic salts or kojic derivatives. The mouth-pasting agent comprises a tooth-adhering layer and a backing layer, wherein the tooth-adhering layer contains a water-soluble polymer such as polyvinylalcohol and the backing layer contains a water-insoluble polymer such as ethyl cellulose. However, polyvinylalcohol has a poor tooth-adhering property. Also, since all of the used whitening agents have strong acidity, they can cause irritation in accordance with pH in the mouth.

U.S. Pat. No. 5,425,953, filed by the Perio Company, discloses a sustained-release film-forming liquid polymer composition comprising a water-soluble cellulose polymer such as hydroxypropyl cellulose, a peroxy compound, a peroxy compound-stabilizing agent such as EDTA and a solvent such as water or ethanol. The liquid polymer composition, which is in a film-forming formulation at the tooth surface, can attribute stabilization of the peroxy compound, but can cause irritation in the other mucous membranes in the mouth before the liquid composition forms a film.

U.S. Pat. Nos. 6,419,906, 6,503,486 and 6,514,483, granted to the Colgate Company, disclose film formulations prepared by mixing polyethylene oxide with peroxides. However, use of only polyethylene oxide does not give sufficient adhering ability to the teeth surfaces to the film. In addition, the film is rapidly solubilized in the mouth and thus does not guarantee a sufficient time for release of the peroxide in a desired amount. Furthermore, since the film is composed of only a tooth-adhering layer, it often adheres to the mucous membranes as well as the teeth, and thus is very inconvenient.

Korean Pat. Laid-open Publication Nos. 10-2002-96264, 10-2002-97297, 10-2002-97298, 10-2003-299, 10-2003-1297 and 10-2003-3973, applied by the LG Household & Health Care Ltd., disclose dry-type patches for tooth whitening, which are prepared by mixing a hydrophilic polymer such as polyvinylpyrrolidone with peroxides, a peroxide-stabilizing agent and the like. In order to prepare such dry-type patches, a tooth-adhering layer and a backing layer are required. The tooth-adhering layer contains a hydrophilic polymer, which cannot adhere to the teeth surfaces or has a weak adhesive strength under a dry condition, and, when the whitening agent is applied to a desired area of the teeth and then hydrated by a small amount of water thereon, come to have an ability to adhere to the teeth surfaces or a strong adhesive strength. The backing layer is composed of essentially a water-insoluble polymer such as ethyl cellulose to protect the tooth-adhering layer. However, these kinds of patches are inconvenient in use since they must be removed after being applied to the teeth during a prescribed time. Also, the patches require caution in use due to the following reason. When hydration makes very rapid progress and thus, the patches loses adhesive strength, the whole or a portion of the backing layer may be detached from the patches and stick in one's throat, thereby causing safety risks.

As described above, because of comprising a backing layer, the conventional patches associated with tooth whitening have several disadvantages including inconvenience of being essentially removed from the teeth after use during a prescribed period, safety risks caused by its weakened adhesive strength capable of leading the water-insoluble backing layer detached from the applied teeth to be caught in the esophagus or airway, and obstruction sensation in the teeth or the mouth.

Thus, through a thorough and intensive research, the present inventors prepared a patch for tooth whitening by employing polymer complexes having an erosion property of various rates. Research resulted in the finding that the patch has a tooth-whitening effect identical to the conventional tooth whitening patches as well as being eroded and eventually completely distinguished on the teeth after use, thereby solving the inconvenient problem requiring separate removal of the patch from its applied teeth.

SUMMARY OF THE INVENTION

It is therefore an object of the present invention to provide a patch for tooth whitening, which is extinguished by erosion in a proper erosion rate after releasing a peroxide tooth whitening substance during a prescribed period.

EXPLANATION OF SYMBOL TO MAIN PART OF THE DRAWING

Figure 1:
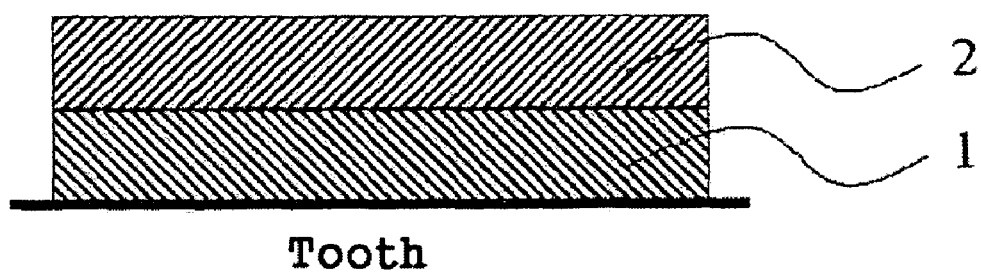
FIG. 1 is a cross-sectional view of a patch for tooth whitening according to the present invention.

1: a tooth-adhering layer
2: an erosion rate-controlling layer.

DETAILED DESCRIPTION OF THE INVENTION

The present invention provides a patch for tooth whitening, comprising a tooth-adhering layer (1) containing erodible polymer complexes formed by hydrogen bonding of a polymer with a carboxyl group (—COOH) and a polymer with a carbonyl group (—C═O) or ether group (—O—) and a tooth whitening agent; and an erosion rate-controlling layer (2) containing a mixture of a hydrophilic polymer and a film-forming polymer.

The patch for tooth whitening is in a film form, and is characterized by being eroded until extinguished after releasing the tooth whitening agent.

The present invention will be described in detail as follows.

The patch for tooth whitening according to the present invention comprises a tooth-adhering layer containing erodible polymer complexes formed by hydrogen bonding of a polymer with a carboxyl group (—COOH) and a polymer with a carbonyl group (—C═O) or ether group (—O—) and a tooth-whitening agent.

The said tooth-adhering layer releases a tooth-whitening agent upon adherence to the teeth surfaces.

In the present invention, the erodible polymer complexes refer to polymer complexes formed by an intermolecular bonding (hydrogen bonding, ionic bonding or Vanderwaals force) of two kinds of polymers, that is, a polymer with a carboxyl group (—COOH) and a polymer with a carbonyl group (—C═O) or ether group (—O—). These complexes are characterized by adhering to the teeth surfaces, solubilized or swollen by water, such as saliva, after being adhered to the teeth during a prescribed period and then gradually eroded until extinguished. Also, the complexes can form a film.

Therefore, in the patch for tooth whitening of the present invention, the tooth-adhering layer has a hydrophilic property and better adhesive strength and film-forming ability.

The hydrogen boding forming the edible polymer complexes of the present invention is a strong attraction between a hydrogen atom bound to an atom of high electronegativity in one molecule and an atom of high electronegativity in another molecule. When hydrogen bonding is formed between polymers, the polymer chains are cross-linked and thus do not freely move.

The physical cross-linking such as hydrogen bonding is reversible according to solvents, temperature and hydrogen ion concentration, and may control solubility of the polymers in a solution. Also, since the binding strength between polymers varies according to the kinds of polymers participating hydrogen bonding, the cross-linking can control dissolution or erosion rates of the polymers. In contrast, cross-linked polymers by a general chemical method have physical properties of not being dissolved in a solvent but just being swollen therein.

The polymer with a carboxyl group used in the tooth-adhering layer includes polyacrylic acid, polymethacrylic acid, (meth)acrylic acid such as Carbopol and Carbofil (BF Goodrich Company), a (meth)acrylic acid copolymer (EUDRAGIT (Meth)acrylate copolymer L, EUDRAGIT (Meth)acrylate copolymer S, KOLLICOAT Methacrylic acid/ethyl acrylate copolymer P) such as EUDRAGIT (Meth)acrylate copolymer (Rohm Pharma Company), a poly alkyl vinyl ether-maleic acid copolymer such as Gantrez (ISP Corporation), alginic acid, hyaluronic acid and mixtures thereof. In particular, the (meth)acrylic acid copolymer is preferable.

The (meth)acrylic acid copolymer is selected from the group consisting of EUDRAGIT (Meth)acrylate copolymer L (methacrylic acid: methyl methacrylate=1:1, Rohm Pharma Company), Eudfagit EUDRAGIT (Meth)acrylate copolymer S (methacrylic acid: methyl methacrylate=1:2, Robin Pharma Company), EUDRAGIT (Meth)acrylate copolymer L 100-55 (methacrylic acid: ethyl acrylate=1:1, Rohm Pharma Company), and KOLLICOAT Methacrylic acid/ethyl acrylate copolymer MAE (methacrylic acid: ethyl acrylate=1:1, BASF). In particular, EUDRAGIT (Meth) acrylate copolymer L (methacrylic acid: methyl methacrylate=1:1) is preferable.

The polymer with a carbonyl group or ether group used in the tooth-adhering layer includes polyvinylpyrrolidone, polyethylene oxide, polypropylene oxide, and a polypropylene oxide-polyethylene oxide copolymer such as Pluronic (BASF Corporation). In particular, the polyvinylpyrrolidone is preferable due to its properties of having better film-forming ability and adhesive strength and of greatly attributing the stability of peroxides by forming complexes with the peroxides in a solution.

The tooth-adhering layer of the present invention may allow formation of various erodible polymer complexes from the polymer with a carboxyl group and the polymer with a carbonyl group or ether group. In particular, polymer complexes composed of the (meth)acrylic acid copolymer and the polyvinylpyrrolidone are most preferable.

The tooth-adhering layer of the present invention contains the polymer with a carboxyl group in an amount of 1-10% by weight of the total dry weight of the tooth-adhering layer. If the content of the polymer with a carboxyl group is less than 1% by weight, it forms a very weak cross-linking with the polymer with a carbonyl group or ether group, causing the film to be rapidly eroded and eventually extinguished by solubilization within several minutes. If the content of the polymer with a carboxyl group is higher than 10% by weight, the cross-link density becomes greatly increased, resulting in swelling of the tooth-adhering layer by saliva and thus causing obstruction sensation in the mouth.

In addition, the tooth-adhering layer of the present invention contains the polymer with a carbonyl group or ether group in an amount of 40-80% by weight of the total dry weight of the tooth-adhering layer. If the content of the polymer with a carbonyl group or ether group is less than 40% by weight, the tooth-adhering layer has poor adhesive strength to the teeth. If the content is higher than 80% by weight, the polymer with a carbonyl group or ether group is difficult to form polymer complexes with the polymer with a carboxyl group.

Solubilization of the erodible polymer complexes by saliva in the mouth can be controlled by the ratio of the two polymers in the erodible polymer complexes, that is, polymer-polymer complexes formed by hydrogen bonding of the polymer with a carboxyl group and the polymer with a carbonyl group or ether group. Therefore, in the patch of the present invention, the tooth-adhering layer can possess a desired adherence time when applied to the teeth.

The patch for tooth whitening according to the present invention further comprises an erosion rate-controlling layer containing a hydrophilic polymer and a film-forming polymer.

The said erosion rate-controlling layer functions to control the erosion rate of the tooth-adhering layer and minimizing obstruction sensation caused by the swelling of the tooth-adhering layer, as well as being composed of non-adhesive polymers and thus being capable of preventing the patch for tooth whitening from adhering to the mucous membranes other than the teeth surfaces.

Preferably, the hydrophilic polymer used in the erosion rate-controlling layer is hydroxypropyl cellulose, and the film-forming polymer is a (meth)acrylic acid copolymer.

The hydroxypropyl cellulose is well dissolved in water and can thus control the erosion rate of the tooth-adhering layer. Also, when the hydroxypropyl cellulose is mixed with the (meth)acrylic acid copolymer, a hard film is formed with no stickiness.

The content of the hydroxypropyl cellulose ranges from 10% to 60% by weight of the total dry weight of the erosion rate-controlling layer. If the content is less than 10% by weight, the erosion rate is reduced. In contrast, if the content is higher than 60% by weight, the erosion rate-controlling layer is eroded very rapidly.

In addition, since the (meth)acrylic acid copolymer is not dissolved in acidic water but is slowly dissolved in a pH range higher than pH 6, it is desirable as a film-forming polymer.

The content of the (meth)acrylic acid copolymer ranges from 5% to 65% by weight of the total dry weight of the erosion rate-controlling layer. If the content is less than 5% by weight, the erosion rate-controlling layer is eroded and eventually extinguished before sufficiently releasing a whitening agent. In contrast, if the content is higher than 65% by weight, the erosion rate-controlling layer is not eroded, even after a long-term period of adherence to the teeth surfaces.

In the patch of the present invention, the erosion rate-controlling layer has a solubilization rate that varies according to the mixing ratio of the two polymers while forming a transparent water-permeable membrane, thereby making it possible to control the erosion rate of the patch for tooth whitening.

The patch for tooth whitening of the present invention contains a peroxide compound as a tooth whitening agent in the tooth-adhering layer. The said peroxide is one or more selected from the group consisting of hydrogen peroxide, carbamide peroxide, calcium peroxide, sodium percarbonate, sodium perborate and tetrasodium pyrophosphate peroxidate. In the present invention, the hydrogen peroxide is preferable. The content of the peroxide ranges from 0.1% to 10% by weight of the total dry weight of the tooth-adhering layer. If the content is less than 0.1% by weight, a desired whitening effect is not obtained. In contrast, if the content is higher than 10% by weight, safety risks can be caused, including erosion of the teeth surfaces and damage of the mucous membranes in the mouth.

In addition, the patch for tooth whitening according to the present invention may further comprise a plasticizer, a peroxide-stabilizing agent and a condensed polyphosphate, which are commonly used in the art.

The patch for tooth whitening should be easily transformed according to the shape of the teeth when directly adhered to the teeth. In this regard, the plasticizer is used to give flexibility to the patch. The plasticizer may vary depending on the kinds of the polymers, and may include one or more selected from the group consisting of propylene glycol, glycerol, triethylcitrate, sorbitol and polyethylene glycol.

The said peroxide-stabilizing agent is used for stability of the peroxide compound in the patch during storage, and may include one or more selected from the group consisting of ethylenediaminetetraacetic acid (EDTA), citric acid, DEQUEST polyphosphate phosphonates, sorbitan monolaurate (SML), sorbitan monopalmitate (SMP), sorbitan stearate, sorbitan monooleate (SMO), sorbitan oleate, sorbitan trioleate and POE sorbitan fatty acid ester surfactants.

The said condensed polyphosphate is used in combination with the peroxide compound to improve the whitening effect of the patch. The said condensed polyphosphate attributes the stability of the peroxide compound, and are effective in removing the dental tartar or preventing formation of the tartar. In addition, the polyphosphate, which is as a good chelating agent for metals, is effective in the removal of the tooth stains caused by food or metals present in the working environments, such as iron, calcium and magnesium. The condensed polyphosphate may include one or more selected from the group consisting of sodium metaphosphate, sodium hexametaphosphate, tetrasodium pyrophosphate, sodium acid pyrophosphate, sodium tripolyphosphate and potassium metaphosphate.

The patch for tooth whitening of the present invention may further comprise a fluoride ion to prevent tooth decay, or a stannous ion to reduce gingivitis or plaque.

Fluorine-containing compounds include sodium fluoride, potassium fluoride, stannous fluoride, monofluoride phosphate (MFP) and ammonium fluoride.

Tin-containing compounds include stannous fluoride, stannous acetate, stannous gluconate, stannous oxalate, stannous malonate, stannous citrate, stannous ethylene glycoside and stannous formate.

The patch for tooth whitening may still further comprise a pigment with various colors, flavoring agent, a sweetening agent and a moistening agent.

The pigment is used to make the teeth whiter, and selected from the group consisting of titanium dioxide, talc, hydroxyapatite, zinc oxide and mixtures thereof.

Examples of the flavoring agent include peppermint, spearmint, wintergreen, sage, eucalyptus oil, methylsalicylate and other fruit extracts.

Examples of the sweetening agent and moistening agent include mannitol, xylitol, lactose, aspartame and saccharin sodium.

The patch for tooth whitening of the present invention, preferably, has a thickness ranging from 50 to 300 μm. In particular, preferably, the tooth-adhering layer has a thickness ranging from 30 to 200 μm, and the erosion rate-controlling layer has a thickness ranging from 20 to 100 μm. If the thickness of the patch is less than 50 μm, the skin irritation is caused by the peroxide whitening agent. If the patch has a thickness exceeding 300 μm, it is very thick, causing obstruction sensation in the mouth. In this case, the patch is detached by the tongue, and it is difficult for the patch to adhere to the teeth for a long period.

The patch for tooth whitening of the present invention, which is composed of the tooth-adhering layer and the erosion rate-controlling layer, remains adhered to the teeth surfaces for about 30 min to 3 hrs according to the composition of the two layers and the ratio of the polymers therein, and thereafter gradually eroded until extinguished.

In addition, since the tongue's movement can affect the erosion of the patch for tooth whitening, the patch can maintain adherence to the teeth surfaces about 5 to 8 hrs more while the user is sleeping than during mental and physical activities, and thereafter gradually eroded until extinguished.

The patch for tooth whitening may be in various forms comprising a tooth-adhering layer and an erosion rate-controlling layer. That is, the patch of the present invention may have a multi-layered structure comprising a tooth-adhering layer containing a tooth whitening agent and a plurality of erosion rate-controlling layers having different erosion rates.

The patch for tooth whitening of the present invention is prepared by the following procedure.

For a tooth-adhering layer, a homogenous solution is prepared by dissolving polyvinylpyrrolidone, (meth)acrylic acid copolymer, polyethylene glycol, hydrogen peroxide, sorbitan monolaurate, sodium acid pyrophosphate and peppermint in a mixture of water and ethanol.

For an erosion rate-controlling layer, a homogenous coating solution is prepared by dissolving hydroxypropyl cellulose, a (meth)acrylic acid copolymer, polyethylene glycol, sorbitan monolaurate and peppermint in ethanol.

After removing bubbles from the said prepared solutions for tooth-adhering layers and erosion rate-controlling layers, a PET film (SK) is coated with each of the solutions using a coating apparatus, and dried at 40 to 80° C., and preferably, 60° C.

The two films are laminated using a compressing roller, and dried at 40 to 80° C., thus yielding a patch for tooth whitening in a film form.

The present invention will be explained in more detail with reference to the following examples. However, the following examples are provided only to illustrate the present invention, and the present invention is not limited to the examples.

EXAMPLES 1 to 9

Preparation of Patches for Tooth Whitening According to the Present Invention

In order to provide patches for tooth whitening in double-layered polymer complex film forms, coating solutions for the formation of tooth-adhering layers and erosion rate-controlling layers were prepared using the compounds listed in Table 1, below, and patches were prepared using the coating solutions.

1. Preparation of Solutions for Tooth-Adhering Layers

Polyvinylpyrrolidone, a (meth)acrylic acid copolymer, polyethylene glycol, hydrogen peroxide, sorbitan monolaurate, sodium acid pyrophosphate and peppermint were dissolved in amounts listed in Table 1, below, in a mixture of water and ethanol, thus giving homogenous solutions.

2. Preparation of Solutions for Erosion Rate-Controlling Layers

Hydroxypropyl cellulose, a (meth)acrylic acid copolymer, polyethylene glycol, sorbitan monolaurate and peppermint were dissolved in amounts listed in Table 1, below, in ethanol, thus giving homogenous coating solutions.

3. Preparation of Patches

In each case, after removing bubbles from the said prepared solutions for tooth-adhering layers and erosion rate-controlling layers, a PET film (SK) was coated with each of the solutions using a coating apparatus (Mathis Dry Coater), and dried at 40 to 80° C., and preferably, 60° C.

The two films were laminated using a compressing roller, and dried at 60° C., thus yielding a patch for tooth whitening in a film form.

Herein, the film had a thickness of 100 to 150 μm.

A cross-sectional view of the patch for tooth whitening of is given in FIG. 1.

In Examples 1 to 3, the tooth-adhering layer was prepared with various ratios of polyvinylpyrrolidone to (meth)acrylic acid copolymer.

In Examples 4 to 9, the erosion rate-controlling layer was prepared with various ratios of hydroxypropyl cellulose to (meth)acrylic acid copolymer.

TABLE 1

| | | Example (wt, g) | | | | | | | | |
|---|---|---|---|---|---|---|---|---|---|---|
| | Composition | 1 | 2 | 3 | 4 | 5 | 6 | 7 | 8 | 9 |
| Tooth-adhering layer | Polyvinylpyrrolidone | 15 | 15.8 | 14 | 15 | 15 | 15 | 15 | 15 | 15 |
| | (meth)acrylic acid copolymer | 1 | 0.2 | 2 | 1 | 1 | 1 | 1 | 1 | 1 |
| | Polyethylene glycol | 4 | 4 | 4 | 4 | 4 | 4 | 4 | 4 | 4 |

TABLE 1-continued

| | Composition | Example (wt, g) | | | | | | | | |
|---|---|---|---|---|---|---|---|---|---|---|
| | | 1 | 2 | 3 | 4 | 5 | 6 | 7 | 8 | 9 |
| | Hydrogen peroxide (35%) | 2.6 | 2.6 | 2.6 | 2.6 | 2.6 | 2.6 | 2.6 | 2.6 | 2.6 |
| | Sorbitan monolaurate | 1 | 1 | 1 | 1 | 1 | 1 | 1 | 1 | 1 |
| | Sodium acid pyrophosphate | 0.1 | 0.1 | 0.1 | 0.1 | 0.1 | 0.1 | 0.1 | 0.1 | 0.1 |
| | Peppermint | 0.2 | 0.2 | 0.2 | 0.2 | 0.2 | 0.2 | 0.2 | 0.2 | 0.2 |
| | Distilled water | 19 | 19 | 19 | 19 | 19 | 19 | 19 | 19 | 19 |
| | Ethanol | 57.1 | 57.1 | 57.1 | 57.1 | 57.1 | 57.1 | 57.1 | 57.1 | 57.1 |
| Erosion rate-controlling layer | Hydroxypropyl cellulose | 10.4 | 10.4 | 10.4 | 18.6 | 15.8 | 12.8 | 8.0 | 5.2 | 2.5 |
| | (meth)acrylic acid copolymer | 9.6 | 9.6 | 9.6 | 1.4 | 4.2 | 7.2 | 12.0 | 14.8 | 17.5 |
| | Polyethylene glycol | 6 | 6 | 6 | 6 | 6 | 6 | 6 | 6 | 6 |
| | Sorbitan monolaurate | 0.8 | 0.8 | 0.8 | 0.8 | 0.8 | 0.8 | 0.8 | 0.8 | 0.8 |
| | Peppermint | 0.2 | 0.2 | 0.2 | 0.2 | 0.2 | 0.2 | 0.2 | 0.2 | 0.2 |
| | Ethanol | 73 | 73 | 73 | 73 | 73 | 73 | 73 | 73 | 73 |

COMPARATIVE EXAMPLE 1

A patch for tooth whitening was prepared according to the same method and with the same composition as in Example 1, except for no addition of (meth)acrylic acid copolymer upon preparation of a tooth-adhering layer.

COMPARATIVE EXAMPLE 2

A patch for tooth whitening was prepared according to the same method as in Example 1, except for no addition of (meth)acrylic acid copolymer and use of polyethylene oxide instead of polyvinylpyrrolidone upon preparation of a tooth-adhering layer.

COMPARATIVE EXAMPLE 3

A patch for tooth whitening was prepared according to the same method as in Example 1, except for no addition of (meth)acrylic acid copolymer and use of hydroxypropylmethyl cellulose instead of polyvinylpyrrolidone upon preparation of a tooth-adhering layer.

COMPARATIVE EXAMPLE 4

A patch for tooth whitening was prepared according to the same method and with the same composition as in Example 1, except for no addition of hydrogen peroxide as a tooth whitening agent upon preparation of a tooth-adhering layer.

COMPARATIVE EXAMPLE 5

A patch for tooth whitening was prepared in a form without an erosion rate-controlling layer, where a tooth-adhering layer was prepared by using the same composition as in Example 1.

The compositions of Comparative Examples 1 to 5 are given in Table 2, below.

TABLE 2

| | Composition | Comparative Example (wt, g) | | | | |
|---|---|---|---|---|---|---|
| | | 1 | 2 | 3 | 4 | 5 |
| Tooth-adhering layer | Polyvinylpyrrolidone | 15 | — | — | 15 | 15 |
| | Polyethylene oxide | — | 15 | — | — | — |
| | Hydroxypropylmethyl cellulose | — | — | 15 | — | — |
| | (Meth)acrylic acid copolymer | — | — | — | 1 | 1 |
| | Polyethylene glycol | 2 | 2 | 2 | 2 | 2 |
| | Hydrogen peroxide (35%) | 2.6 | 2.6 | 2.6 | — | 2.6 |
| | Sorbitan monolaurate | 1 | 1 | 1 | 1 | 1 |
| | Sodium acid pyrophosphate | 0.1 | 0.1 | 0.1 | 0.1 | 0.1 |
| | Peppermint | 0.2 | 0.2 | 0.2 | 0.2 | 0.2 |
| | Distilled water | 19.1 | 19.1 | 19.1 | 20.7 | 18.1 |
| | Ethanol | 60 | 60 | 60 | 60 | 60 |
| Erosion rate-controlling layer | Hydroxypropyl cellulose | 10.4 | 10.4 | 10.4 | 10.4 | — |
| | (Meth)acrylic acid copolymer | 9.6 | 9.6 | 9.6 | 9.6 | — |
| | Polyethylene glycol | 6 | 6 | 6 | 6 | — |
| | Sorbitan monolaurate | 0.8 | 0.8 | 0.8 | 0.8 | — |
| | Peppermint | 0.2 | 0.2 | 0.2 | 0.2 | — |
| | Ethanol | 73 | 73 | 73 | 73 | — |

EXPERIMENTAL EXAMPLE 1

Measurement of Adherence Time to the Teeth of the Patches for Tooth Whitening of the Present Invention In order to investigate the degree of erosion and disappearance of the patch for tooth whitening of the present invention according to time, adherence time of the patches to the teeth surfaces was measured.

Test pieces for the upper teeth were obtained from the patches prepared in the Examples 1 to 9 and Comparative Examples 1 to 5, and applied to the teeth of subjects.

A commercially available patch for tooth whitening (trade name: Claren; LG Household & Health Care Ltd.) was used as Control 1, which comprises a tooth-adhering layer containing polyvinylpyrrolidone and hydrogen peroxide and a backing layer containing ethyl cellulose and castor oil.

Another commercially available patch for tooth whitening (trade name: Whitestrips; P&G Company) was used as Control 2, which comprises a tooth-adhering layer in a carbomer gel form containing hydrogen peroxide and a backing layer in a polyethylene film.

The test results are given in Table 3, below.

TABLE 3

|   | Adherence time (min) | | | | | |
|---|---|---|---|---|---|---|
|   | 30 | 60 | 90 | 120 | 150 | 180 |
| E. 1 | Shape maintained | Shape maintained | Shape maintained | Partial loss | Complete loss | — |
| E. 2 | Shape maintained | Shape maintained | Complete loss | — | — | — |
| E. 4 | Partial loss | Complete loss | — | — | — | — |
| E. 5 | Shape maintained | Partial loss | Complete loss | — | — | — |
| E. 6 | Shape maintained | Shape maintained | Partial loss | Complete loss | — | — |
| E. 7 | Shape maintained | Shape maintained | Shape maintained | Shape maintained | Partial loss | Complete loss |
| E. 8 | Shape maintained | Shape maintained | Shape maintained | Shape maintained | Partial loss | Complete loss |
| E. 9 | Shape maintained | Shape maintained | Shape maintained | Shape maintained | Shape maintained | Partial loss |
| C.E. 1 | Detached from the teeth | — | — | — | — | — |
| C.E. 2 | Shape maintained | Detached from the teeth | — | — | — | — |
| C.E. 3 | Shape maintained | Detached from the teeth | — | — | — | — |
| C.E. 5 | Complete loss | — | — | — | — | — |
| Control 1 | Lasting adherence to the teeth | Lasting adherence to the teeth | Lasting adherence to the teeth | Lasting adherence to the teeth | Detached from the teeth | — |
| Control 2 | Lasting adherence to the teeth | Lasting adherence to the teeth | Lasting adherence to the teeth | Detached from the teeth | — | — |

As shown in Table 3, when the erosion rate-controlling layer was prepared with various ratios of hydroxypropyl cellulose to (meth)acrylic acid copolymer, the patches for tooth whitening were found to adhere to the teeth for a longer period (Examples 4 to 9). In particular, the adherence abilities of the patches were found to increase with the content of the (meth)acrylic acid copolymer.

In addition, the patches for tooth whitening according to the present invention (Examples 1 to 9, except for 3) were found to remain adhered to the teeth for a longer time than the cases of applying Comparative Examples 1 to 3. These results are believed to originate from the hydrogen bonding leading to polymer complexes in the tooth-adhering layer.

In the case of being composed of only a tooth-adhering layer (Comparative Example 5), the patch was eroded and eventually completely extinguished before sufficiently releasing the whitening agent, and adhered to the mucous membranes other than the teeth in the mouth, causing inconvenience in use.

Also, the tooth whitening patches of the present invention were eroded until extinguished about 30 min to 3 hrs after application to the teeth. In contrast, in case of using the patch of Control 1 in which the backing layer contains ethyl cellulose, the patch remained adhered to the teeth for over 2 hrs and then come off from the teeth about 3 hrs after application. In case of using the patch of Control 2 in which the backing layer is composed of a polyethylene film, the patch remained adhered to the teeth for about 1 hr 30 min and then come off from the teeth about 2 hrs after application. In these cases, the tooth-adhering layer maintains its adhesive strength to the teeth during its components are not completely solubilized, and, when its components are completely solubilized, it slowly losses its adhesive strength. Consequently, the backing layer remains on the teeth surfaces, and must be removed from the teeth by the hands, thereby causing inconvenience in use.

Taken together, the patch for tooth whitening of the present invention has a controllable erosion rate and adherence time to the teeth by combination of the polymers and composition change of the tooth-adhering layer and the erosion rate-controlling layer. Especially, the adherence time to the teeth was found to increase with the content of the (meth)acrylic acid copolymer in the erosion rate-controlling layer.

EXPERIMENTAL EXAMPLE 2

Assay for Whitening Effect of the Patches for Tooth Whitening of the Present Invention The tooth whitening patches of the present invention were evaluated for whitening effect, as follows.

15 teeth were removed from persons not having tooth decay, divided into three groups, and used as specimens for evaluation of whitening effect of the patches.

The initial L value (L is a brightness and represented by from 100 (white) to 0 (black)) of each specimen was measured using a color reader. The patches for tooth whitening, prepared in Example 1, Control 1 and Comparative Example 4, were adhered to the wet specimen, and incubated under a condition similar to that in the mouth, that is, at an incubator at 37° C. under a humidity of 95%. After a prescribed time, the patches were detached from the specimens, washed with running water while rubbed with a paste brush, and then dried at room temperature.

The above procedure was repeated for two weeks. During this test period, L values were measured before and after application of the patches to the teeth. The difference between the values before and after the application of the patches, that is, ΔL was calculated. The results are given in Table 4, below.

TABLE 4

|  | ΔL |
| --- | --- |
| E. 1 | 4.07 ± 0.97 |
| Control 1 | 3.08 ± 0.67 |
| C.E. 4 | 0.13 ± 0.26 |

As shown in Table 4, the patches for tooth whitening of the present invention (Example 1 and Control 1), which contains a tooth whitening agent, were found to be superior to the patch not containing the tooth whitening agent (Comparative Example 4).

EXPERIMENTAL EXAMPLE 3

Evaluation of Convenience or Inconvenience in Use of the Patches for Tooth Whitening of the Present Invention The tooth whitening patches of the present invention were evaluated for obstruction sensation in the mouth, as follows.

The patches of the present invention, prepared in Example 1 and 3, and the Controls 1 and 2 patches were adhered to the upper teeth of subjects, and then obstruction sensation was investigated.

The results are given in Table 5, below.

TABLE 5

|  | Obstruction sensation upon adherence to the teeth |
| --- | --- |
| E. 1 | 1 |
| E. 3 | 2 |
| Control 1 | 3 |
| Control 2 | 3 |

Note:
1: rare
2: slight
3: unpleasant
4: very severe

As shown in Table 5, when adhering the patch prepared in Example 1 to the teeth, the subjects rarely felt an obstruction sensation. Also, the patch prepared in Example 3 caused a slight obstruction sensation in the mouth by swelling of the tooth-adhering layer, where the swelling is driven by cross-linking of polyvinylpyrrolidone and (meth)acrylic acid copolymer by hydrogen bonding.

In contrast, the patches of Controls 1 and 2 caused unpleasant obstruction sensations. Also, in these cases, there were a chilly sensation on the teeth and bitter taste.

When applied to the teeth, the patch for tooth whitening according to the present invention is solubilized and then eroded until extinguished after releasing a peroxide compound, thereby reducing an unpleasant feeling of a foreign body. In addition, because of being solubilized by water in the mouth, the patch of the present invention is very convenient in use.

As described hereinbefore, the patch for tooth whitening according to the present invention, when applied to the teeth, releases a peroxide tooth-whitening agent while being hydrated by water in the mouth during a prescribed period, and thereafter, eroded until extinguished, thereby not requiring an additional detaching work from the teeth. Therefore, the patch of the present invention is convenient in use and greatly reduces an obstruction sensation. Moreover, the patch has an excellent whitening effect.

What is claimed is:

1. A patch for tooth whitening, comprising
a tooth-adhering layer (1) containing erodible polymer complexes formed by hydrogen bonding of a first polymer with a carboxyl group (—COOH) and a second polymer with a carbonyl group (—C=O) or ether group (—O—) and a tooth whitening agent,
wherein the first polymer comprises from 1% to 10% of the total dry weight of the tooth-adhering layer, and the second polymer comprises from 40% to 80% of the total dry weight of the tooth-adhering layer; and
wherein the first polymer with the carboxyl group is a (meth)acrylic acid copolymer, and the second polymer with the carbonyl group or ether group is polyvinylpyrrolidone; and
an erosion rate-controlling layer (2) containing a mixture of a hydrophilic polymer and a film-forming polymer, wherein the hydrophilic polymer ranges from 10% to 60% of the total dry weight of the erosion rate-controlling layer and the film-forming polymer ranges from 5% to 65% of the total dry weight of the erosion rate-control layer; and
wherein the hydrophilic polymer is hydroxypropyl cellulose and the film-forming polymer is a (meth) acrylic acid copolymer.

2. The patch as set forth in claim 1, wherein the first polymer of the tooth-adhering layer is selected from the group consisting of poly(methacrylic acid-co-methyl methacrylate) copolymer with a monomer molar ratio of 1:1, poly(methacrylic acid-co-methyl methacrylate) copolymer with a monomer molar ratio of 1:2, and poly)methacrylic acid-co-ethyl acrylate) copolymer with a monomer molar ratio of 1:1.

3. The patch as set forth in claim 1, wherein the film-forming polymer of the erosion rate-controlling layer is selected from the group consisting of poly(methacrylic acid-co-methyl methacrylate) copolymer with a monomer molar ratio of 1:1, poly(methacrylic acid-co-methyl methacrylate) copolymer with a monomer molar ratio of 1:2, and poly(methacrylic acid-co-ethyl acrylate) copolymer with a monomer molar ratio of 1:1.

4. The patch as set forth in claim 1, wherein the tooth whitening agent in the tooth-adhering layer is selected from the group consisting of hydrogen peroxide, carbamide peroxide, calcium peroxide, sodium percarbonate, sodium perborate and tetrasodium pyrophosphate peroxidate.

5. The patch as set forth in claim 1, further comprising a plasticizer which is selected from the group consisting of propylene glycol, glycerol, triethylcitrate, sorbitol and polyethylene glycol.

6. The patch as set forth in claim 1, further comprising a peroxide-stabilizing agent which is selected from the group consisting of ethylenediaminetetraacetic acid (EDTA), citric acid, polyphosphates, phosphonates, sorbitan monolaurate (SML), sorbitan monopalmitate (SMP), sorbitan stearate, sorbitan monooleate (SMO), sorbitan oleate, sorbitan trioleate and POE sorbitan fatty acid ester surfactants.

7. The patch as set forth in claim 1, further comprising a condensed polyphosphate which is selected from the group consisting of sodium metaphosphate, potassium metaphosphate, sodium hexametaphosphate, tetrasodium pyrophosphate, sodium acid pyrophosphate and sodium tripolyphosphate.

8. The patch as set forth in claim 1, wherein a thickness of the patch ranges from 50 μm to 300 μm.

9. The patch as set forth in claim 8, wherein the tooth-adhering layer has a thickness of 30 μm to 200 μm, and the erosion rate-controlling layer has a thickness of 20 μm to 100 μm.

10. The patch as set forth in claim 1, further comprising polyethylene glycol in the tooth-adhering layer, wherein the polyethylene glycol comprises 4 weight % of the total weight of the tooth-adhering layer prior to drying.

11. The patch as set forth in claim 1, further comprising polyethylene glycol in the erosion rate-controlling layer, wherein the polyethylene glycol comprises 6 weight % of the total weight of the erosion rate-controlling layer prior to drying.

12. The patch as set forth in claim 1, wherein the tooth-adhering layer is dried at 40° C. to about 80° C.

13. The patch as set forth in claim 1, wherein the erosion-controlling layer is dried at about 40° C. to about 80° C.

14. The patch as set forth in claim 1, wherein the tooth-adhering layer and the erosion-controlling layer are laminated.

15. The patch as set forth in claim 14, wherein the laminated tooth-adhering layer and erosion-controlling layer is dried at 40° C. to 80° C.

16. The patch as set forth in claim 1, wherein the patch erodes from about 30 minutes to about 3 hours after application to the teeth.

* * * * *